(12) United States Patent
Bergman et al.

(10) Patent No.: US 7,565,802 B2
(45) Date of Patent: Jul. 28, 2009

(54) HIGH PRESSURE PRESSING DEVICE AND A METHOD

(75) Inventors: Carl Bergman, Västerås (SE); Mats Gärdin, Västerås (SE)

(73) Assignee: Avure Technologies AB, Vasteras (SE)

( * ) Notice: Subject to any disclaimer, the term of this patent is extended or adjusted under 35 U.S.C. 154(b) by 597 days.

(21) Appl. No.: 10/518,961

(22) PCT Filed: Jun. 24, 2003
(Under 37 CFR 1.47)

(86) PCT No.: PCT/SE03/01084

§ 371 (c)(1),
(2), (4) Date: Dec. 8, 2005

(87) PCT Pub. No.: WO04/000451

PCT Pub. Date: Dec. 31, 2003

(65) Prior Publication Data

US 2007/0144587 A1    Jun. 28, 2007

(30) Foreign Application Priority Data

Jun. 24, 2002    (SE) .................................... 0201924

(51) Int. Cl.
*F15B 7/00*     (2006.01)
*A23L 3/00*     (2006.01)
(52) U.S. Cl. ........................................ 60/486; 426/665
(58) Field of Classification Search ................ 60/486; 426/665; 137/565.33
See application file for complete search history.

(56) References Cited

U.S. PATENT DOCUMENTS

| | | | | |
|---|---|---|---|---|
| 3,869,241 A | 3/1975 | David et al. | ............ | 425/405 H |
| 4,279,581 A | 7/1981 | Betz | ............. | 425/78 |
| 5,213,029 A * | 5/1993 | Yutaka | ............. | 99/474 |
| 5,370,043 A * | 12/1994 | Traff et al. | ............. | 99/467 |
| 5,579,682 A * | 12/1996 | Bergman et al. | ............. | 99/473 |
| 5,765,465 A * | 6/1998 | Gardin et al. | ............. | 92/86 |
| 5,891,505 A * | 4/1999 | Schuman et al. | ............. | 426/665 |
| 5,993,172 A | 11/1999 | Schuman et al. | ............. | 417/394 |
| 6,162,392 A | 12/2000 | Platz et al. | ............. | 422/26 |
| 7,096,774 B2 * | 8/2006 | Hellgren | ............. | 92/86 |

FOREIGN PATENT DOCUMENTS

| | | |
|---|---|---|
| DE | 199 16 478 A1 | 10/2000 |
| EP | 0 480 422 A2 | 4/1992 |
| EP | 0 772 981 A1 | 5/1997 |
| FR | 2 442 018 | 6/1980 |
| JP | 1-171553 | 7/1989 |
| JP | 3-114523 | 5/1991 |
| JP | 3-236765 | 10/1991 |
| JP | 4-96753 | 3/1992 |
| JP | 6-277267 | 10/1994 |
| WO | WO 94/21145 | 9/1994 |

\* cited by examiner

*Primary Examiner*—Thomas E Lazo
(74) *Attorney, Agent, or Firm*—Harness, Dickey & Pierce PLC

(57) ABSTRACT

A pressing device and a method of providing a change of pressure between two pressure states: a low pressure state and a high pressure state of at least 4000 bar, in a pressure vessel of a high pressure isostatic pressing device in which a liquid pressure medium is used for generating the pressure. A first pressure changing device is used for changing the pressure from one of two pressure states to an intermediate pressure state, and a second pressure changing device is used for changing the pressure from the intermediate pressure state to the other one of the two pressure states.

24 Claims, 4 Drawing Sheets

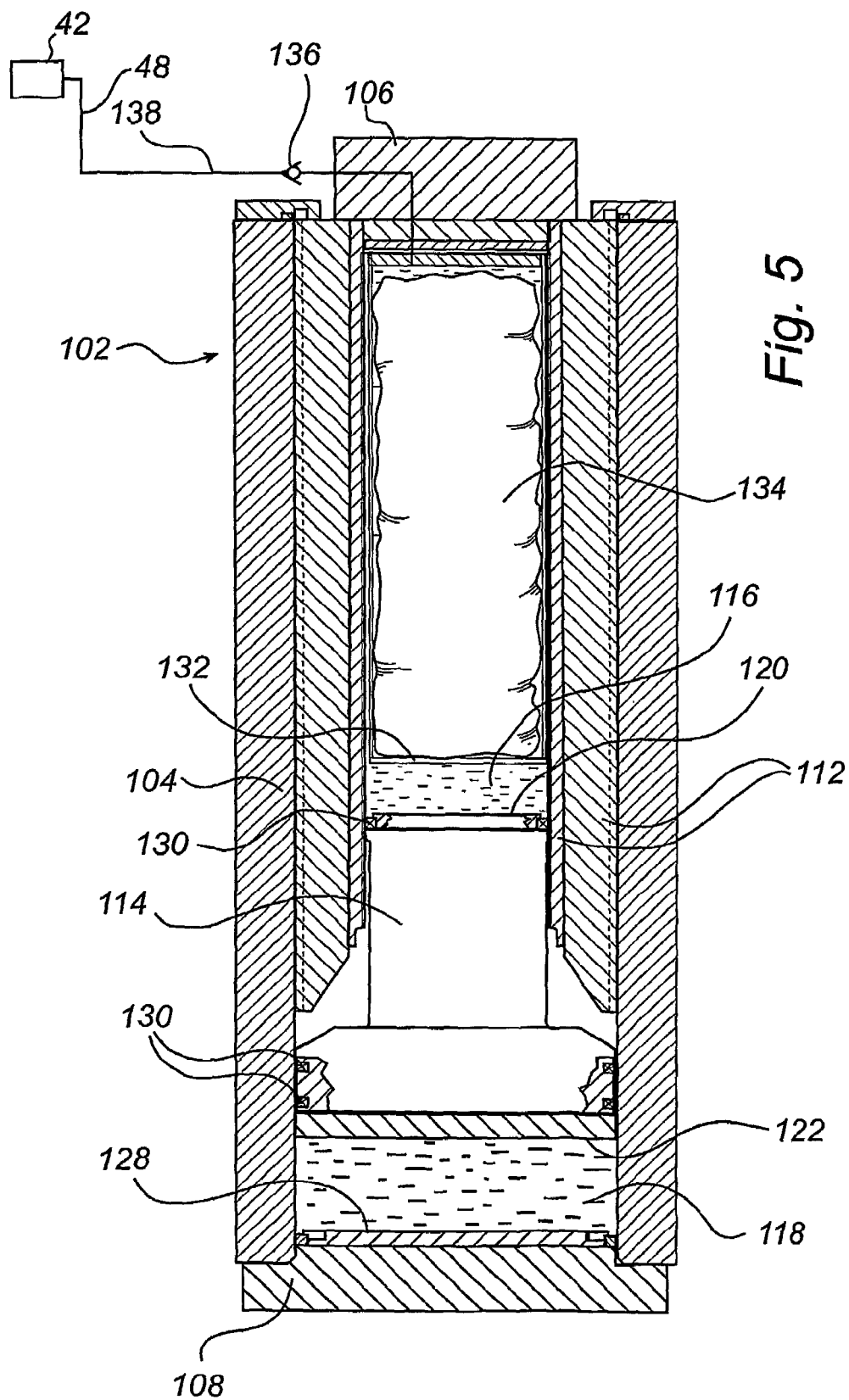

HIGH PRESSURE PRESSING DEVICE AND A METHOD

CROSS-REFERENCE TO RELATED APPLICATION

This application is the National Stage of International Application No. PCT/SE2003/001084, filed on Jun. 24, 2003.

BACKGROUND OF THE INVENTION

1. Field of the Invention

The present invention relates to a high pressure isostatic pressing device and a method of providing a change of pressure between two pressure states in a high pressure isostatic pressing device in which a liquid pressure medium is used for generating the pressure. In particular, the invention concerns generation of pressure of at least 4000 bar.

2. Description of the Related Art

High pressure presses, in which a liquid pressure medium is used for generating isostatic high pressures, may be utilized for pressing different types of loads. For instance, high pressure presses are used for compacting powdered graphite or ceramic, or for treating foodstuffs. In certain applications, such as in treatment of foodstuffs, it is desirable to generate a pressure of about 6000 bar in the pressure vessel of the high pressure press in order to ensure the inactivating effect on micro-organisms and enzymes.

Standard hydraulic pumps of today can only be practically utilized to generate a pressure of about 4000 bar. The reason for this is inter alia dimensional limitations, such as fatigue limit of the materials of the pumps. Typically, steel is a construction material in these types of pumps and is subjected to considerable fatigue at the desirable high pressure level. Furthermore, the mechanical stress on certain components, such as valves and piping intersection points, would be very large at said high pressure level. If such a pump would be forced to generate a pressure of 6000 bar one or more components would soon break, already after a low number of pressure cycles.

One possible way to avoid the drawbacks mentioned above would be to use a single-stroke pressure intensifier, which has the advantage of having fewer components and being subjected to few press cycles. This means that its working life is considerably longer than the above mentioned standard pumps and thus achieves a better reliability. However, the disadvantage is that, for a single-stroke pressure intensifier to generate 6000 bar, it will be a large, bulky and expensive construction. Therefore, such a single-stroke pressure intensifier is most unpractical and is seldom used.

Another problem arises when the pressure vessel is to be decompressed after a finished pressing operation, i.e. when the liquid pressure medium is to be removed so as to obtain access to the pressed load inside the pressure vessel. To decompress the pressure vessel from 6000 bar to ambient pressure involves great wear and some fatigue on the release or decompression valve as the liquid pressure medium rushes at high speed past the valve.

BRIEF SUMMARY OF THE INVENTION

An object of the present invention is to provide a method and a high pressure pressing device which alleviate the above mentioned drawbacks.

Another object of the present invention is to increase the operational reliability for a high pressure press of the previously described type.

Yet another object of the present invention is to provide a high pressure pressing device which has low operating costs.

A further object of the present invention is to provide a high pressure pressing device that comprises components having a large service life.

These and other objects, which will become apparent in the following, are achieved by a method and a high pressure pressing device as defined in the accompanied claims.

One aspect of the invention concerns a method of providing a change of pressure between two pressure states (a low pressure state and a high pressure state, the high pressure state being at least 4000 bar) in a pressure vessel of a high pressure isostatic pressing device in which a liquid pressure medium is used for generating the pressure. According to the method liquid pressure medium, such as hydraulic oil or water, is transferred between a first pressure changing device and the pressure vessel, thereby changing the pressure in the pressure vessel from one of said pressure states to an intermediate pressure state which has a value between the pressures of the two pressure states. Thereafter, liquid pressure medium is transferred between a second pressure changing device and the pressure vessel, thereby changing the pressure in the pressure vessel from said intermediate pressure state to the other one of said pressure states.

Another aspect of the invention concerns a high pressure isostatic pressing device which comprises a pressure vessel and a pressure changing arrangement. The pressure changing arrangement is adapted to transfer liquid pressure medium between the pressure changing device and the pressure vessel in the corresponding manner as disclosed in the method above. The high pressure pressing device of the invention is typically used for cold isostatic pressing.

The invention is based on the insight that it is possible in a high pressure pressing device to generate a high pressure, such as 6000 bar, by splitting the generation of pressure into two separate steps, performed by two pressure changing devices so that standby costs and maintenance costs may be reduced considerably. For example costs for spare parts, work, loss of production and products that need to be discarded, are reduced. The intermediate pressure may e.g. be about 2000 bar or above, and may even be up to 85% of the final high pressure.

Accordingly, for pressing a load a liquid pressure medium is fed into the pressure vessel. This is suitably performed by the first pressure changing device, which is also used for pressurizing the liquid pressure medium. However, a separate or additional feeding device may also be used in the initial filling of the pressure vessel. The pressurized liquid pressure medium causes the pressure vessel to be subjected to said intermediate pressure, which is lower than the final high pressure. Thereafter, the second pressure changing device is used for intensifying the pressure of the liquid pressure medium so that the pressure in the pressure vessel is increased from said intermediate pressure state to the high pressure state.

The pressure vessel and the second pressure changing device may be arranged in fluid communication with each other. This arrangement allows a portion of the liquid pressure medium that has been fed into the pressure vessel to be led or bled from the pressure vessel to the second pressure changing device. In this case the volume to be filled by the liquid pressure medium fed to the pressure vessel includes the volume of the pressure vessel and the volume of a space in the second pressure changing device. Said space may e.g. include a pressure chamber in the second pressure changing device and a conduit from said pressure chamber to the pressure vessel. Even though this is a practical arrangement, it is to be understood that others are also possible. Said space in the second pressure changing device may be filled with liquid pressure medium from another source, and thus not necessarily via the pressure vessel.

Regardless of how the space in the second pressure changing device is filled, the liquid pressure medium therein will be forced (returned or forwarded) into the pressure vessel. At the same time such liquid pressure medium which is already present inside the pressure vessel is prevented from escaping from the pressure vessel, thereby causing a further build-up of pressure in the pressure vessel so that the load is expediently pressed.

The invention is also based on the insight that it is possible in a high pressure pressing device to decompress from a high pressure, such as 6000 bar, to a low pressure, such as atmospheric pressure, by splitting the decompression of pressure into two separate steps, performed by two pressure changing devices. This will considerably reduce the mechanical wear due to cavitation and abrasion caused by rushing liquid pressure medium, and thus by having two pressure changing devices, they will instead be subjected to relatively low and manageable wear. Wear is very pressure dependent and as will be illustrated with an example later on, it is for instance possible to use a pressure intensifier to withdraw liquid from the pressure vessel. In such a case the low pressure side of the intensifier is throttled and controlled at e.g. about 300 bar instead of e.g. about 6000 bar at a release valve in connection with the pressure vessel.

Accordingly, for decompressing the pressure vessel after a load has been pressed the used liquid pressure medium is removed from the pressure vessel. This is done by first withdrawing a portion of the liquid pressure medium from the pressure vessel to the first pressure changing device, causing the pressure in the pressure vessel to be lowered from the prevailing high pressure to said intermediate pressure.

Once a portion of the liquid pressure medium has been withdrawn from the pressure vessel, as a first decompressing step, the rest of the liquid pressure medium is released from the pressure vessel to the second pressure changing device. This causes the pressure in the pressure vessel to be decreased from said intermediate pressure state to the low pressure state.

In the first decompressing step, the volume of withdrawn liquid pressure medium should generally correspond to the volume of the liquid pressure medium which was forced into the pressure vessel when the pressure therein was increased from the intermediate pressure state to the high pressure state for pressing a load inside the pressure vessel. However, it is to be understood that the introduced volume of liquid pressure medium (for changing from intermediate to high pressure state) may differ from said withdrawn volume (for changing from high to intermediate pressure state). One important factor is that both volumes are large enough so as to reduce strain on sensitive components outside the pressure vessel.

Furthermore, it is possible to have one pressure changing device for changing from the intermediate to the high pressure state and another pressure changing device for changing from the high to the intermediate pressure state. From the above it should be clear that the second pressure changing device used during pressurization and the first pressure changing device used during decompression may, but does not have to, be one and the same pressure changing device.

After the two steps have been performed, i.e. withdrawing a portion and releasing the rest of the liquid pressure medium from the pressure vessel, the withdrawn portion may either be disposed of directly or may be pumped, via the pressure vessel, over to the second pressure changing device used for the releasing step. The advantage of this is that the entire used liquid pressure medium is collectable at one common place. It may also be kept in the single-stroke intensifier for the next cycle.

In a typical pressing operation the low pressure state prevails when the pressure vessel is substantially decompressed, i.e. at ambient or atmospheric pressure. This is the case when there is substantially no liquid pressure medium present in the pressure vessel. However, the low pressure state may alternatively be regarded as the state in which a volume of liquid pressure medium that corresponds to the free volume inside the pressure vessel has been supplied to the pressure vessel (and any space of the intensifying second pressure changing device in communication with the pressure vessel), i.e. when the pressure vessel has been filled but before any extra liquid pressure medium is forced into the pressure vessel for generating an increase of pressure. The low pressure state may also be regarded as a pressure which is applied before the actual pressing operation, in order to eliminate any remaining air bubbles which have not been removed during an initial deaeration step. This type of initial filling or bubble elimination is not to be regarded as a pressure stage in the context of the teachings of this application.

It is to be noted that when increasing the pressure from the low pressure state to the intermediate pressure state, this may be done in several partial stages. Anyhow, said increase is achieved by means of said first pressure changing device, which e.g. may comprise a standard hydraulic pumping system with one or several pumps.

The high pressure state typically means the maximum pressure level of the current pressing operation at which the load in the pressure vessel is pressed. As previously mentioned, for treatment of foodstuffs the high pressure state or the actual operating state would be at a level of about 6000 bar or possibly even higher.

The liquid pressure medium used is generally water, though other liquids are also possible to use, such as e.g. oil. The liquid pressure medium may even be the actual substance to be treated.

A multifunctional pressure changing device that has been found appropriate for the implementation of the present invention is a small single-stroke intensifier. The single-stroke intensifier will have two main functions. One function is, in pressurization, to increase the pressure in the pressure vessel from an intermediate pressure such as 3000-4000 bar to the isostatic operating high pressure such as 6000 bar. The other function is, in decompression, to decrease the pressure in the pressure vessel, after a terminated pressing of a load therein, from the operating high pressure such as 6000 bar to an intermediate pressure such as 3000-4000 bar.

The use of a single-stroke intensifier relieves and saves the standard hydraulic pump and the sensitive components therein from being impaired prematurely, by taking over the responsibility of the pressurization at an acceptable pressure level. The standard hydraulic pump does not have to be forced to pressure levels that have adverse affect on the material of the pump, but is instead only operated to an intermediate pressure level, thereby ensuring a long service life. Also, pistons in a standard hydraulic pump are provided with seals for preventing liquid from passing from one chamber to another. The pistons are displaced back and forth many times at high pressure during pressurization, which causes the seals to be quickly worn out. Obviously, the less the pistons are displaced at high pressure the less will be the wear of the seals. Since the increase from the intermediate pressure state to the operating high pressure state is performed by a single-stroke intensifier, any seals provided on a piston in such an intensifier will only be subjected to a single advancing motion at high pressure during the pressurization. The standard hydraulic pumps are, apart from application in high pressure presses, also used for water jet cutting. A typical standard hydraulic pump which may be used is 7X provided by Flow International Cooperation.

The single-stroke intensifier which is used to subsequently increase the pressure in the pressure vessel from the intermediate pressure level such as 3000-4000 bar to the isostatic operating high pressure such as 6000 bar, may be dimensioned to have a relatively small stroke volume, which may be about a fifth of the volume needed if a bulky single-stroke intensifier would be used to generate in one stroke the high pressure starting from atmospheric pressure. The reason for this is that the compressibility of water decreases as the pressure rises, i.e. the higher the pressure is in the pressure vessel, the less extra volume of liquid pressure medium is needed for further increasing the pressure a determined range. This relationship is shown in the accompanied FIG. 4 of the drawings. This means that for reaching half the value of the final operating high pressure a larger volume of liquid pressure medium is transferred into the pressure vessel than for the subsequent increase of pressure. Thus, the single-stroke intensifier benefits from the fact that a standard hydraulic pump manages to pressurize the pressure vessel up to quite a large degree, allowing the single-stroke intensifier to be of small size.

The single-stroke intensifier comprises a low pressure cylinder in which a low pressure piston is axially displaceable. On one side of the low pressure cylinder and coaxially therewith, a high pressure cylinder is arranged. A high pressure piston is secured to the low pressure piston and is arranged axially displaceable in the high pressure cylinder. The high pressure cylinder is in fluid communication with the pressure vessel. Liquid pressure medium will be led into the space in the high pressure cylinder. When the pressure in the pressure vessel is to be raised from the intermediate pressure state to the high pressure state, a pressure medium, such as oil, will be supplied into the low pressure cylinder. This will cause the pistons to be driven towards the high pressure cylinder and the liquid pressure medium present therein will be forced out therefrom and into the pressure vessel.

Another advantage of the single-stroke intensifier is that it enables an easy pressure reduction in the pressure vessel, before opening a release valve in order to let out the rest of the liquid pressure medium from the pressure vessel. The reduction to the intermediate high pressure is achieved by drawing off the hydraulic (oil) pressure medium in the low pressure cylinder, thereby releasing the counter pressure against the pressure vessel and allowing the pistons to be moved towards the low pressure cylinder and the high pressure cylinder will be filled with liquid pressure medium from the pressure vessel. The pressure in the pressure vessel has now returned to the intermediate pressure state. The release valve will be subjected to considerably less wear, when it decompresses from 3000-4000 bar instead of from 6000 bar.

Yet another advantage of the present invention is that a traditional safety valve for 6000 bar may be replaced by a safety valve for only about 200 bar connected to the low pressure cylinder of the single-stroke intensifier. A safety valve for 6000 bar is pretty much for one-time use. Due to the large pressure and flow speed, cavitation problems will occur and rapidly destroy the safety valve. In the present invention the safety valve will open for the moderate pressure of 200 bar and drain some hydraulic pressure medium from the low pressure cylinder of the single-stroke intensifier, enabling the pistons to be displaced towards the low pressure side. This means an increase in volume available for the pressurized liquid pressure medium present in the pressure vessel and the high pressure side of the single-stroke intensifier, wherein the pressure is reduced and held at the safety level. The safety valve on the low pressure side may be a conventional overflow valve adapted to hold a pressure of 200 bar, or of course if desirable a higher pressure, such as 300-500 bar.

Just like the safety valve, a draining valve used for reducing the pressure to the intermediate pressure state may be any valve that is dimensioned for pressures of a couple of hundred bar. Thus, after a finished pressing operation, the draining valve, arranged at the low pressure side of the single-stroke intensifier, is opened so as to drain the hydraulic pressure medium from the low pressure cylinder, thereby decreasing the pressure in the pressure vessel to the intermediate pressure state.

Furthermore, it follows from the above that the pressure may be measured on the low pressure side of the single-stroke intensifier, instead of using a pressure gauge at the pressure vessel.

From the above, it is clear that, when a single-stroke intensifier is used, it functions as said first pressure changing device in a decompressing act, and as said second pressure changing device in a pressurization act. This double functionality underlines the advantage of using a single-stroke intensifier.

As an alternative, it would be possible to use two or more single-stroke intensifiers, instead of just one. In such a case they would be operated in parallel or one after the other. One advantage is that the standard hydraulic pump does not even have to generate a pressure of 3000-4000 bar, but a lower value would suffice. Correspondingly, in the decompression operation, the single-stroke intensifiers would enable an effective lowering of pressure in the pressure vessel to a value below 3000-4000 bar. The release valve is thereby even more protected from damage.

The connection between the single-stroke intensifier and the pressure vessel may have different dimensions. It may be a narrow conduit or it may be coupling having a large cross-section. The connection or coupling may even be as wide as the pressure vessel and/or the single-stroke intensifier. In fact, the pressure intensifier and the pressure vessel may be integrated as a unit. In the high pressure chamber of the single-stroke intensifier a high pressure piston is displaceable between a retracted position and an advanced position. The pressure vessel may therefore be regarded as a front portion of the high pressure chamber of the single-stroke intensifier, i.e. substantially the portion that is left for the liquid pressure medium when the high pressure piston is in the advanced position providing an increased pressure, relative to the retracted position, in the high pressure chamber. The rest of the high pressure chamber, i.e. the portion extending between the retracted position and advanced position of the high pressure piston, may be regarded as comprising a pressure changing device in which the piston is movable. Thus, in the case of pressurization said portion would correspond to the second pressure changing device as previously described. In the case of decompression, said portion would correspond to the first pressure changing device. The connection between the single-stroke intensifier and the pressure vessel corresponds in this case to the wall of the single-stroke intensifier. Even though the above example is an integrated unit, it is also possible to connect two separate units, i.e. a single-stroke intensifier and a pressure vessel, which have substantially the same internal cross-section. The invention solves the problem of compressibility of liquid pressure medium regardless of the volume of the pressure vessel, which may be a small pressure vessel, such as 30 dm$^3$, or a large pressure vessel, such as 300 dm$^3$. In either case, an extra volume in addition to the total volume of the pressure vessel, is to be forced into the pressure vessel to attain the operating high pressure state. This extra volume is a defined percentage of the total volume.

From what has been described above, it should be clear that the present invention provides an efficient way of pressurizing a pressure vessel of a high pressure pressing device, and an efficient way of decompressing it. The fundamental feature of the invention is that the pressure in one and the same pressure vessel is changed in two separate steps. Thus, it is not a question of raising in one pressure vessel the pressure of a medium, which is to be forwarded and further raised in another pressure vessel. It is however a question of using two pressure changing devices in connection with one common pressure vessel.

It should also be clear from the above that in accordance with the invention great consideration is shown for material strength of the components in the high pressure pressing device. According to the invention the standard hydraulic pump is only operated to generate up to a pressure which permits a long service life thereof. The same applies to the release valve, which is only opened at a pressure that does not cause much wear. Furthermore, a single-stroke intensifier is controllable. For instance, if it is only desirable to increase the pressure to a certain level, which is below the pressure level that is possible to achieve with a full stroke of the single-stroke intensifier, a shorter stroke may be used. The same applies to the act of decompressing, wherein the pistons of the intensifier may be retracted a shorter distance than the full capacity distance of the intensifier in order to lower the pressure only partly in relation to said full capacity.

BRIEF DESCRIPTION OF THE SEVERAL VIEWS OF THE DRAWINGS

FIG. 5 shows schematically a further embodiment of the present invention.

DETAILED DESCRIPTION OF THE INVENTION

The drawings are merely illustrated for the ease of understanding, and are therefore only schematic and not to scale, for the sake of clarity.

Figure 1:
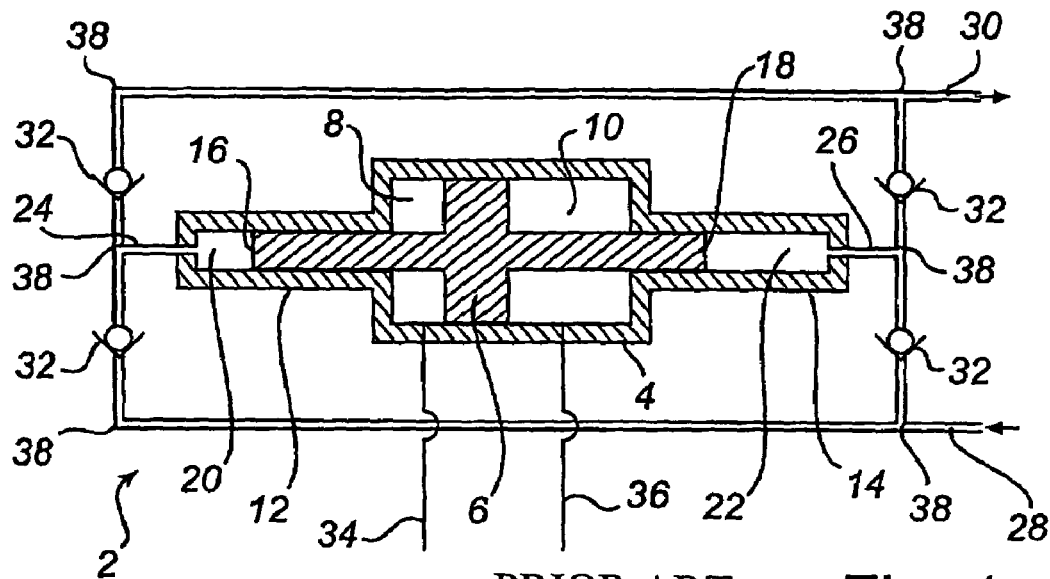
FIG. 1 is a schematic longitudinal section through a prior art standard hydraulic pumping device to be connected to a pressure vessel in which articles are to be pressed.

FIG. 1 is a schematic longitudinal section through a standard hydraulic pumping device 2 according to the prior art. The pumping device 2 comprises a low pressure cylinder 4 in which a low pressure piston 6 is axially displaceable. The low pressure cylinder 4 is thus divided into two sides 8,10 and is filled on both sides with a hydraulic medium. On each side of the low pressure cylinder 4 and coaxially therewith, a respective high pressure cylinder 12,14 is arranged. Each high pressure cylinder 12,14 is provided with a high pressure piston 16,18 which is arranged to be axially displaceable therein. The two high pressure pistons 16,18 are secured to the low pressure piston 6. The two high pressure cylinders 12,14 and the high pressure pistons 16,18 define two high pressure chambers 20,22. Conduits 24,26 are arranged in communication with the high pressure chambers 20,22 for providing liquid pressure medium to flow into and out from the high pressure chambers 20,22. The liquid pressure medium is supplied from an inlet 28 via the conduits to the high pressure chambers 20,22, and is subsequently pumped from the high pressure chambers 20,22 via conduits 24,26 to an outlet 30 connected to the pressure vessel in which articles are to be pressed. The conduits of the standard hydraulic pumping device are provided with four non-return valves 32 for controlling the direction of flow.

For operation of the standard hydraulic pumping device, the low pressure cylinder 4 is provided with two hydraulic connections 34,36 for a hydraulic medium, such as oil, which is supplied by means of a hydraulic unit (not shown). By supplying a quantity of hydraulic medium into the low pressure cylinder 4 on one side 8 of the low pressure piston 6, while at the same time draining the corresponding quantity from the other side 10 of the low pressure piston 6, the pistons 6,16,18 become axially displaced. As one of the high pressure pistons 18 outputs liquid pressure medium from its high pressure chamber 22, the other high pressure chamber 20 is filled with the new liquid pressure medium supplied from the inlet 28 of the pumping device. Next, the pistons 6,16,18 will be caused to move in the other direction so as to output liquid pressure medium at an intensified pressure from the other high pressure chamber 20.

At high pressures some details of the standard hydraulic pumping device 2 may quickly be worn out. Examples are the four non-return valves 32 and sharp corners 38 in the T-couplings and angles of the conduits. Another example are seals (not shown) which are provided on the pistons for preventing liquid from passing from one chamber to another. The seals will during pressurization slide a long distance as the pistons are repeatedly moved back and forth and will therefore wear out in short time. Since there are many sensitive details which are subjected to a pulsating pressure there is a large risk that one of the details will be damaged and will have to be repaired or replaced after only a short time.

Figure 2:
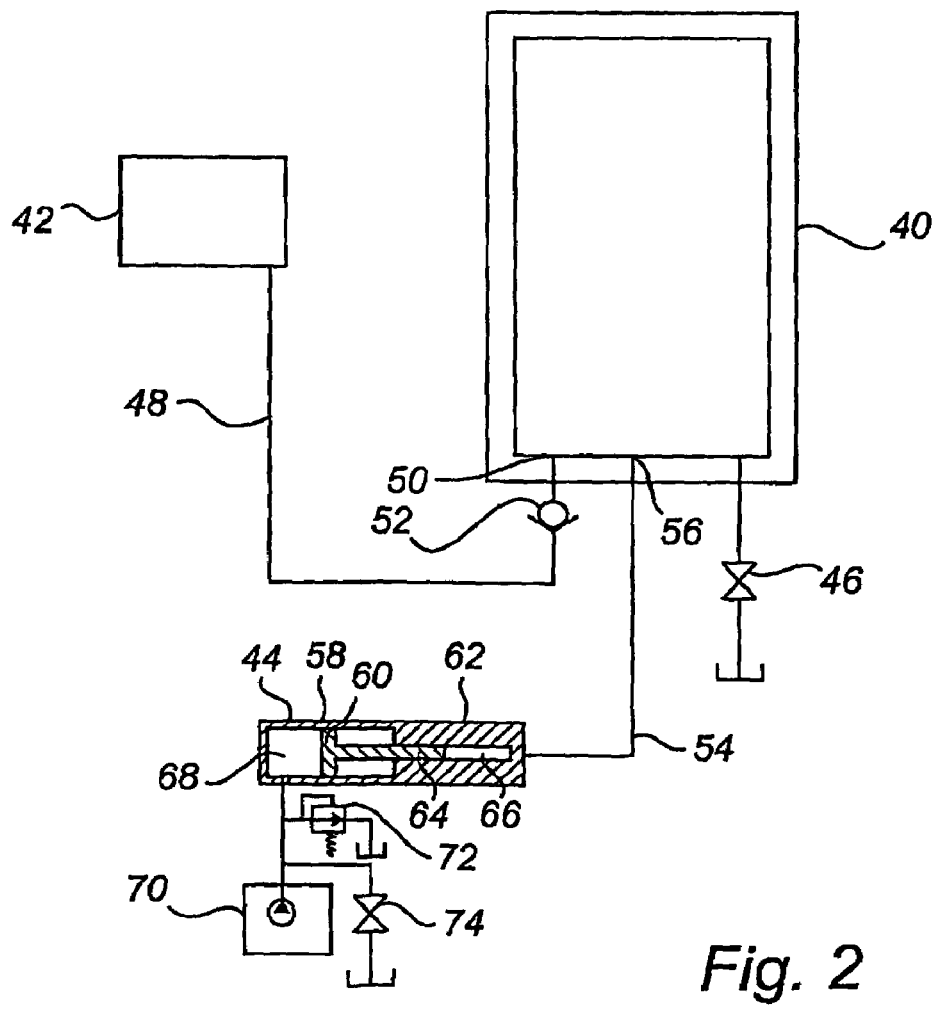
FIG. 2 shows schematically an embodiment illustrating the principle of the present invention.

FIG. 2 illustrates schematically the principle of the present invention. A high pressure pressing device according to the invention comprises inter alia a cylindrical pressure vessel 40 which is designed for handling pressures of 6000 bar, and connected to the pressure vessel 40, a standard hydraulic pumping device 42, a single-stroke intensifier 44 and a release valve 46.

Inside the pressure vessel 40 a load or articles are placed in order to be pressed by means of a liquid pressure medium. The pressure vessel 40 has a volume of 315 liters. The load may e.g. be food, which is suitably contained in a bag. The pressure applied to the bag containing the food is isostatic (equal from all sides) and therefore the food will not experience any distortion. Alternatively, the load may consist of a powder, which can e.g. be metallic, ceramic or graphite. The powder is sealed in a flexible mold shaped like the end product. The powder is subjected to cold isostatic pressing, wherein a high and uniform density is achieved, resulting in easier handling, easier machining and even and predictable shrinking during sintering.

The standard hydraulic pumping device 42 is connected via an outlet conduit 48 to the pressure vessel 40, and may be of the type shown in FIG. 1. Air is removed from the inside of the pressure vessel 40 by suitable means and the pumping device 42 is used for pumping liquid pressure medium into the pressure vessel 40 through a first inlet 50 thereof until a pressure of 4000 bar is reached inside the pressure vessel 40. In order to reach a pressure of 4000 bar an extra volume of 37 dm$^3$ (11.7% of total volume of 315 dm$^3$) is pumped into the pressure vessel 40 after it has been filled. A non-return valve 52 is provided for preventing liquid pressure medium from returning to the pumping device 42.

The single-stroke intensifier 44 is also in fluid communication with the pressure vessel 40 via a conduit 54 connected to a second inlet 56. The single-stroke intensifier 44 comprises a low pressure cylinder 58 in which a low pressure piston 60 is axially displaceable. On one side of the low pressure cylinder 58 and coaxially therewith, a high pressure cylinder 62 is arranged. A high pressure piston 64 is secured to the low pressure piston 60 and is arranged axially displaceable in the high pressure cylinder 62. The high pressure cylinder 62 and the high pressure piston 64 define a high pressure chamber 66. The conduit 54 extends from the high pressure chamber 66 to the second inlet 56 of the pressure vessel 40. When the standard hydraulic pumping device 42 fills the pressure vessel 40 with liquid pressure medium, some liquid pressure medium will also pass through the conduit 54 and fill the high pressure chamber 66 of the single-stroke intensifier 44. This causes the pistons 60,64 to be displaced towards the other end of the low pressure cylinder 58. When the pressure in the pressure vessel 40 is to be raised from the intermediate pressure state of 4000 bar to the high pressure state of 6000 bar, a stroke volume of 10 dm$^3$ (3.2% of total volume of 315 dm$^3$) is used. Additional liquid, such as hydraulic oil or water, will be supplied into the low pressure chamber 68 so as to cause the pistons 60,64 to be driven towards the high pressure cylinder 62 and due to the difference in area between the two pistons 60,64, an intensified pressure will affect the high pressure chamber 66. The liquid pressure medium present in the high pressure chamber 66 will be forced out therefrom and into the pressure vessel 40 via the conduit 54. The conduit 54 between the high pressure chamber 66 and the pressure vessel 40 may be a straight line, without an angle as drawn in FIG. 2. Furthermore, the conduit 54 may have a relatively narrow cross-section or may have a wide cross-section. It may even have a cross-section corresponding to the cross-section of the pressure vessel 40. A variant of that case will be later described in connection with FIG. 5.

Continuing with FIG. 2, the liquid unit 70. There is further provided a safety valve 72 for limiting the pressure in the low pressure chamber 68. For a pressure of 6000 bar in the pressure vessel 40 and the ratio of the diameters of the high pressure piston 64 and the low pressure piston 60 being 1:5, the safety valve 72 is suitably dimensioned to limit the pressure in the for controlling the single-stroke intensifier 44 is supplied from a hydraulic low pressure chamber 68 of the single-stroke intensifier 44 to a pressure level of about 240 bar, corresponding to 6000 bar in the pressure vessel 40. At the predetermined pressure level the safety valve 72 opens and limits the pressure to this level irrespective of the flow through the valve 72. The single-stroke intensifier 44 is also connected to a valve 74 for draining the low pressure chamber 68. Just like the safety valve 72, the draining valve 74 may be any valve that is dimensioned for pressures of a couple of hundred bar. Thus, after a finished pressing operation, the draining valve 74, which may be controllable so as to allow a controlled decompression rate, is opened causing the pistons 60,64 to be retracted in the direction towards the low pressure chamber 68, thereby decreasing the pressure in the pressure vessel 40 to an intermediate pressure state. This is obviously more lenient for the different components than immediately opening the release valve 46, which would be subjected to a pressure of around 6000 bar. Commonly such a release valve includes a tapered shaft which fits into a tapered seat. At such high pressures the shaft will soon become blunt and worn out.

Figure 3:
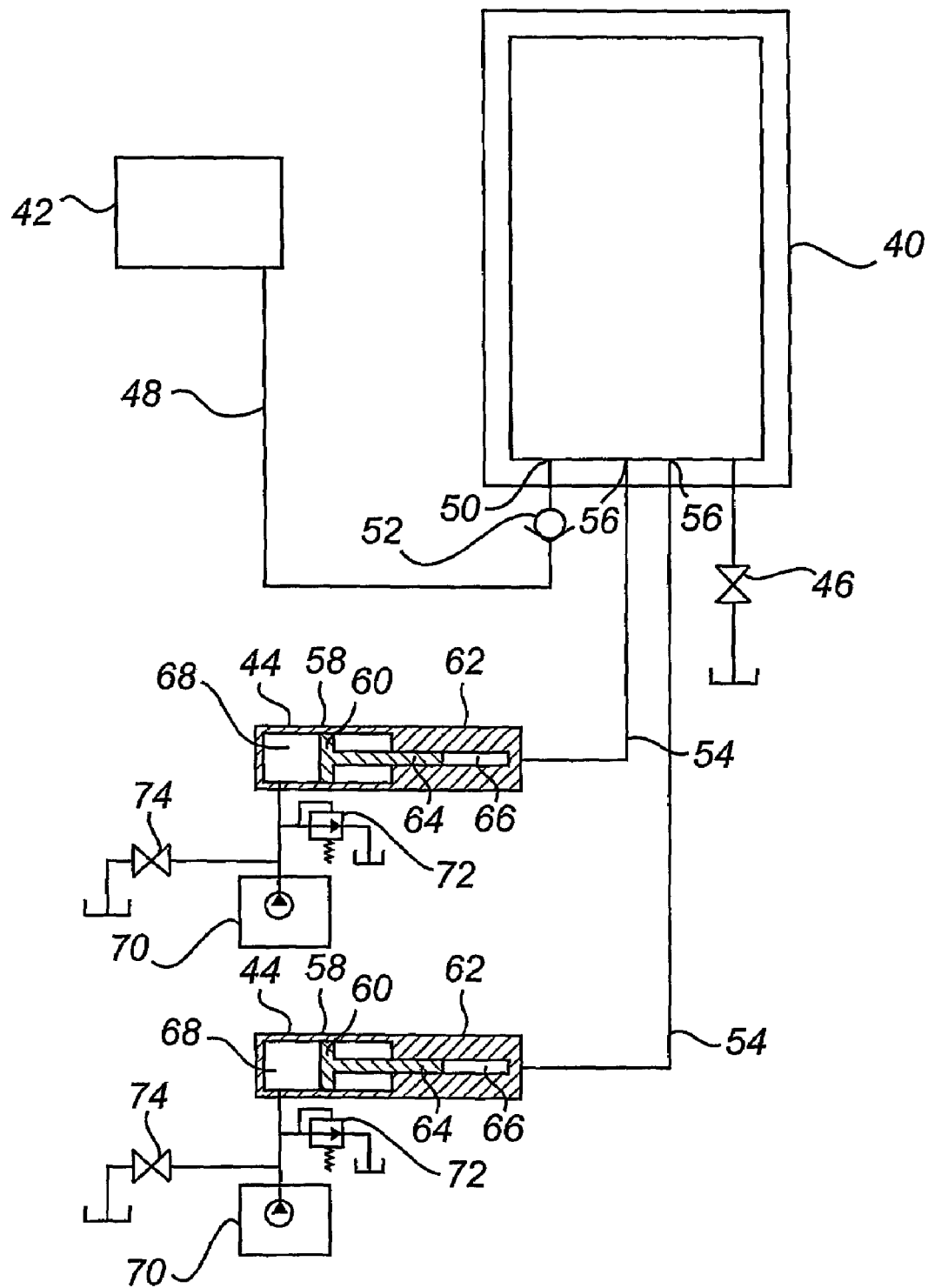
FIG. 3 illustrates an alternative embodiment of the present invention.

FIG. 3 illustrates an arrangement similar to the one in FIG. 2, however, another single-stroke intensifier has been added (same reference numerals are used for corresponding details). The single-stroke intensifier has equal functions and may be operated simultaneously.

Figure 4:
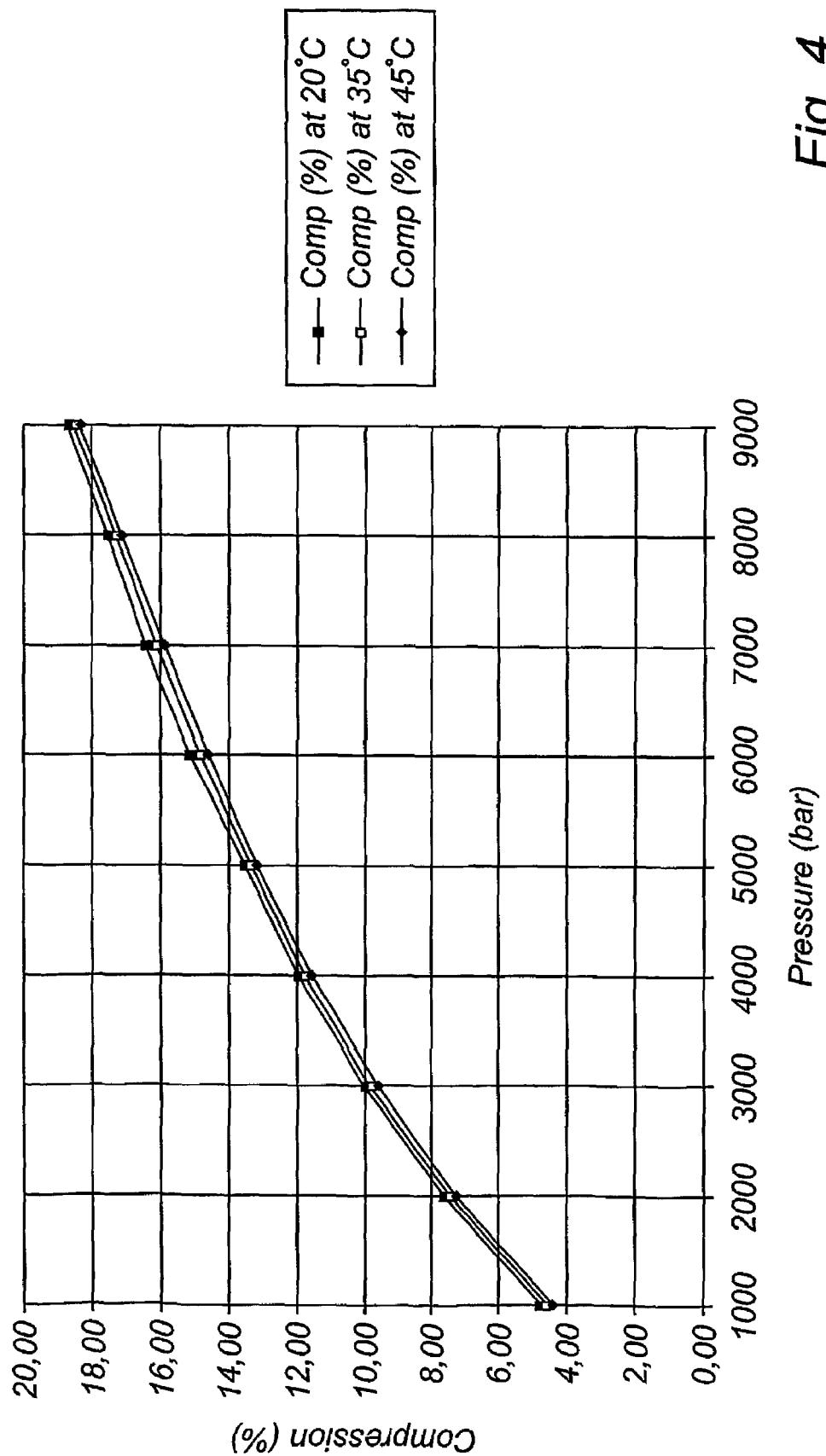
FIG. 4 is a diagram showing the compressibility of water at different start temperatures.

FIG. 4 is a diagram showing the compressibility of water at different start temperatures. The horizontal axis of the diagram indicates the pressure in bar. The vertical axis indicates the compression as a percentage of the total volume of a closed system. For instance, if a pressure vessel holding 100 dm$^3$ has just been filled with water, another 4.5 dm$^3$ of water (i.e. 4.5% of the total volume) is needed to be pumped in, in order to raise the pressure to 1000 bar. As can be seen from FIG. 4, the derivative of the curve decreases as the pressure increases. The present invention takes advantage of this inclination change of the curve. Accordingly, a standard hydraulic pump may be used for pumping the pressure in the pressure vessel to 4000 bar. This means that the standard hydraulic pump inputs an additional 11.7% of the total volume of the system (pressure vessel, high pressure chamber of the intensifier and the conduit therebetween) in order to reach said pressure level. Hence, for reaching the operating pressure of 6000 bar, at which the compression is 14.9%, the single-stroke intensifier only has to input to the pressure vessel 3.2% of the total volume of the pressure vessel. From this it is understood that if only a single-stroke intensifier, without the aid of the standard hydraulic pump, is used, it would require a size almost five times as large as the intensifier used together with the standard hydraulic pump.

FIG. 5 shows schematically a further embodiment of the present invention. A high pressure press in the form of a single-stroke pressure intensifier 102 is shown in longitudinal partial cross-section. The single-stroke intensifier 102 comprises an elongate cylindrical outer wall 104, an upper end cover 106 and a lower end cover 108 at a respective end of the outer wall 104.

The outer wall 104 and the end covers 106, 108 surround inner walls 112 or linings. The outer wall 104 and inner walls 112 or linings define an inner space of the single-stroke intensifier 102. The inner space is, by means of a floating piston device 114, divided into a high pressure chamber 116 and a low pressure chamber 118. The high pressure chamber 116 has a smaller cross-section than the low pressure chamber 118. The floating piston device 114 has a high pressure end 120 with a cross-section corresponding to that of the high pressure chamber 116, and a low pressure end 122 with a cross-section corresponding to that of the low pressure chamber 118.

The floating piston device 114 is displaceable between a completely advanced position and a completely retracted position, which is when its low pressure end 122 abuts the bottom 128 of the low pressure chamber 118.

Displacement of the floating piston device 114 is effected by controlling the amount of hydraulic medium, such as oil or water, present in the low pressure chamber 118. In order to advance the floating piston device 114 more hydraulic medium is fed into the low pressure chamber 118 through a conduit (not shown), and in order to retract the floating piston device 114 hydraulic medium is drained from the low pressure chamber 118.

The floating piston device 114 is provided with seals 130 for preventing medium from leaking from one chamber to the other.

A perforated cage 132 is provided in the high pressure chamber 116 and serves to hold an elastic bag 134 containing e.g. foodstuff, pharmaceuticals, lotions, soaps, cosmetics or any other product to be treated. In said completely advanced position the high pressure end 120 of the floating piston device 114 is situated just below the bottom of the cage 132.

A non-return valve 136 is provided for preventing pressure medium from being returned to the pumping device, similarly to the non-return valve 52 in FIGS. 2 and 3. A liquid medium supply conduit 138 from a standard hydraulic pump leads to said inlet.

In the following the operation of the press will be described. A bag 134 containing foodstuff to be treated is inserted into the cage 132 which is subsequently arranged in place inside the press in the form of a single-stroke intensifier 102, suitably by lowering the cage 132 through the top portion after the upper end cover 106 has been removed. After that the single-stroke intensifier 102 is closed, e.g. by putting the upper end cover 106 in place if it was previously removed. The floating piston device 114 is positioned in its retracted position. Liquid pressure medium is fed from the liquid medium supply conduit 138, through the inlet provided with the non-return valve 136, into the high pressure chamber 116. The liquid medium inside the high pressure chamber 116 will exert an isostatic pressure on the bag 134. Liquid pressure medium is supplied until a pressure of 3000 bar is obtained in the high pressure chamber 116.

Next hydraulic medium is fed into the low pressure chamber 118, thereby forcing the floating piston device 114 to be advanced towards the cage 132 and causing further compression of the liquid pressure medium in the high pressure chamber 116. When the floating piston device 114 has reached its advanced position a pressure of about 6000 bar prevails in the high pressure chamber 116. It is to be understood that for this and any other embodiment of the invention higher pressures are also possible with the same two-step principle. Thus, the inventive concept may be used for generating an even higher pressure, such as e.g. 15000 bar.

After the pressing operation is complete the pressure in the high pressure chamber 116 is first lowered to 3000 bar by retracting the floating piston device 114 and thereafter the rest of the liquid medium is output through an outlet (not shown) having a release valve like the one shown in FIGS. 2 and 3. The bag 134 containing the treated foodstuff is removed after the single-stroke intensifier 102 has been opened.

The high pressure pressing device in FIG. 5 has basically the same function as the high pressure pressing device in FIG. 2. The portion of the high pressure chamber occupied by the cage 132 and the bag 134 in FIG. 5 substantially corresponds to the pressure vessel 40 in FIG. 2. Furthermore, in FIG. 5 the portion between the bottom of the cage 132 and the high pressure end 120 of the floating piston device 114 when in its completely advanced position substantially corresponds to the conduit 54 in FIG. 2. Suitably, the low pressure chamber 118 in FIG. 5 is connected to components corresponding to those components 70, 72, 74 that are connected to the low pressure chamber 68 in FIG. 2. Also, the pressure vessel in FIG. 2 is suitably arranged to receive a cage like the cage 132 shown in FIG. 5.

It is to be understood that even though some specific pressure changing devices have been pointed out, others may be equally possible. Thus, numerous modifications and variations can be made without departing from the scope of the present invention defined in the accompanied claims.

The invention claimed is:

1. A method of providing a change of pressure between two pressure states: a low pressure state and a high pressure state of at least 4000 bar, in a pressure vessel of a high pressure isostatic pressing device in which a liquid pressure medium is used for generating the pressure, the method comprising the steps of:
   transferring liquid pressure medium between a first pressure changing device and the pressure vessel, thereby changing the pressure in the pressure vessel from one of said two pressure states to an intermediate pressure state substantially above atmospheric pressure which has a value between the pressures of the two pressure states; and
   transferring liquid pressure medium between a second pressure changing device and the pressure vessel, thereby changing the pressure in the pressure vessel from said intermediate pressure state to the other one of said two pressure states.

2. The method as claimed in claim 1, for changing the pressure in the pressure vessel from the low pressure state to the high pressure state, wherein
   the first pressure changing device is used for feeding the liquid pressure medium into the pressure vessel, and for pressurizing the liquid pressure medium so that the pressure vessel is subjected to said intermediate pressure being lower than the high pressure, and wherein
   the second pressure changing device is used for intensifying the pressure of the liquid pressure medium so that the pressure in the pressure vessel is increased from said intermediate pressure state to the high pressure state.

3. The method as claimed in claim 2, in which the pressure vessel and the second pressure changing device are arranged in fluid communication with each other, wherein the act of feeding the liquid pressure medium includes bleeding a portion thereof from the pressure vessel into the second pressure changing device.

4. The method as claimed in claim 3, in which the act of intensifying includes the step of forcing bled liquid pressure medium to return into the pressure vessel, while preventing such liquid pressure medium which is already inside the pressure vessel from escaping therefrom.

5. The method as claimed in claim 4, in which said step of forcing is performed in a single stroke by driving a piston of a single-stroke intensifier in a direction from a low pressure side to a high pressure side thereof.

6. The method as claimed in claim 4, in which said second pressure changing device comprises at least two intensifier devices, wherein, for each of the intensifier devices, the step of forcing is performed in a single stroke by driving a piston of a single-stroke intensifier from a low pressure side to a high pressure side thereof.

7. The method as claimed in claim 2, in which the pressure vessel and the second pressure changing device are included in a single-stroke intensifier comprising a high pressure chamber in which a piston is movable between a retracted position and an advanced position, the pressure vessel comprising a first portion of said high pressure chamber extending from the piston when being in its advanced position to an opposing end of the high pressure chamber wall, the second pressure changing device comprising a second portion of said high pressure chamber extending from the retracted position to the advanced position of the piston.

8. The method as claimed in claim 1, for changing the pressure in the pressure vessel from the high pressure state to the low pressure state, such as after a pressing operation, comprising the steps of:
   withdrawing part of the liquid pressure medium from the pressure vessel to the first pressure changing device so that the pressure in the pressure vessel is lowered to said intermediate pressure; and
   releasing the rest of the liquid pressure medium from the pressure vessel to the second pressure changing device so that the pressure in the pressure vessel is decreased from said intermediate pressure to the low pressure.

9. The method as claimed in claim 8, in which the start of said step of releasing is followed by or performed simultaneously by a step of feeding said withdrawn part of the liquid pressure medium from the first pressure changing device via the pressure vessel to the second pressure changing device.

10. The method as claimed in claim 8, in which said step of withdrawing is performed in a single stroke by driving a piston of a single-stroke intensifier from a high pressure side to a low pressure side thereof.

11. The method as claimed in claim 8, in which said first pressure changing device comprises at least two intensifier devices, wherein, for each of the intensifier devices, the step of withdrawing is performed in a single stroke by driving a piston of a single-stroke intensifier from a high pressure side to a low pressure side thereof.

12. The method as claimed in claim 8, in which said second pressure changing device comprises at least one release valve.

13. The method as claimed in claim 8, in which the pressure vessel and the first pressure changing device are included in a single-stroke intensifier comprising a high pressure chamber in which a piston is movable between a retracted position and an advanced position, the pressure vessel comprising a first portion of said high pressure chamber extending from the piston when being in its advanced position to an opposing end of the high pressure chamber wall, the first pressure changing device comprising a second portion of said high pressure chamber extending from the advanced position to the retracted position of the piston.

14. The method as claimed in claim 1, in which said intermediate pressure is in the order of 2000 bar to 85-% of the pressure at said high pressure state.

15. A method of operating a high pressure isostatic pressing device, comprising the steps of:
changing the pressure in a pressure vessel of the high pressure isostatic pressing device, in which a liquid pressure medium is used for generating the pressure, from a low pressure state to a high pressure state of at least 4000 bar;
transferring liquid pressure medium between a first pressure changing device and the pressure vessel, thereby changing the pressure in the pressure vessel from one of said two pressure states to an intermediate pressure state which has a value between the pressures of the two pressure states;
transferring liquid pressure medium between a second pressure changing device and the pressure vessel thereby changing the pressure in the pressure vessel from said intermediate pressure state to the other one of said two pressure states;
using the first pressure changing device for feeding the liquid pressure medium into the pressure vessel, and for pressurizing the liquid pressure medium so that the pressure vessel is subjected to said intermediate pressure being lower than the high pressure;
using the second pressure changing device for intensifying the pressure of the liquid pressure medium so that the pressure in the pressure vessel is increased from said intermediate pressure state to the high pressure state;
withdrawing part of the liquid pressure medium from the pressure vessel to the second pressure changing device so that the pressure in the pressure vessel is lowered to said intermediate pressure state; and
releasing the rest of the liquid pressure medium from the pressure vessel through at least one release valve so that the pressure in the pressure vessel is decreased from said intermediate pressure state to the low pressure state.

16. The method as claimed in claim 15, in which said second pressure changing device comprises or is included in a single-stroke pressure intensifier which comprises a low pressure chamber in which a low pressure piston is axially displaceable, a high pressure chamber being arranged on one side of the low pressure chamber and coaxially therewith, a high pressure piston being secured to the low pressure piston and being arranged axially displaceable in the high pressure chamber, the method further comprising the step of:
measuring the pressure in the low pressure chamber, thereby enabling the pressure in the pressure vessel to be calculated.

17. A high pressure isostatic pressing device for operating at pressures of at least 4000 bar, comprising:
a pressure vessel in which a liquid pressure medium is used for generating a pressure; and
a pressure changing arrangement for providing, in the pressure vessel, a change of pressure between two pressure states: a low pressure state and a high pressure state, the pressure changing arrangement being adapted to transfer liquid pressure medium between a first pressure changing device and the pressure vessel so that the pressure in the pressure vessel is changed from one of said pressure states to an intermediate pressure state substantially above atmospheric pressure which has a value between the pressures of the two pressure states, and to transfer liquid pressure medium between a second pressure changing device and the pressure vessel so that the pressure in the pressure vessel is changed from said intermediate pressure state to the other one of said pressure states.

18. The high pressure pressing device as claimed in claim 17, wherein said first pressure changing device comprises a hydraulic pumping system adapted to increase the pressure in the pressure vessel from the low pressure state to the intermediate pressure state, and wherein said second pressure changing device, being in fluid communication with the pressure vessel, comprises a single-stroke intensifier adapted to increase the pressure in the pressure vessel from the intermediate pressure state to the high pressure state.

19. The high pressure pressing device as claimed in claim 18, wherein said single-stroke intensifier is further adapted to, after a pressing operation, withdraw part of the liquid pressure medium from the pressure vessel so as to decrease the pressure therein from the high pressure state to the intermediate pressure state, and wherein said pressure changing arrangement comprises at least one release valve adapted to release the rest of the liquid pressure medium from the pressure vessel so as to decrease the pressure from the intermediate pressure state to the low pressure state.

20. The high pressure pressing device as claimed in claim 17, wherein said first pressure changing device comprises a single-stroke intensifier which is adapted to withdraw part of the liquid pressure medium from the pressure vessel, thereby decreasing the pressure therein from the high pressure state to the intermediate pressure state, and wherein said second pressure changing device comprises at least one release valve adapted to release the rest of the liquid pressure medium from the pressure vessel, thereby decreasing the pressure from the intermediate pressure state to the low pressure state.

21. The high pressure pressing device as claimed in claim 20, wherein the single-stroke intensifier comprises a low pressure chamber in which a low pressure piston is axially displaceable, a high pressure chamber being arranged on one side of the low pressure chamber and coaxially therewith, a high pressure piston being secured to the low pressure piston and being arranged axially displaceable in the high pressure chamber, wherein a draining valve is provided in communication with the low pressure chamber and may be opened so as to drain fluid from the low pressure chamber and cause said pistons to be retracted in the direction towards the low pressure chamber, thereby decreasing the pressure in the pressure vessel to the intermediate pressure state.

22. The high pressure pressing device as claimed in claim 17, wherein the pressure vessel and one of said pressure changing device are included in a single-stroke intensifier comprising a high pressure chamber in which a piston is movable between a retracted position and an advanced position, the pressure vessel comprising a first portion of said high pressure chamber extending from the piston when being in its advanced position to an opposing end of the high pressure chamber wall, the pressure changing device comprising a second portion of said high pressure chamber extending from the retracted position to the advanced position of the piston.

23. The high pressure pressing device as claimed in claim 18, wherein the single-stroke intensifier comprises a low pressure chamber in which a low pressure piston is axially displaceable, a high pressure chamber being arranged on one side of the low pressure chamber and coaxially therewith, a high pressure piston being secured to the low pressure piston and being arranged axially displaceable in the high pressure chamber, wherein a pressure gauge is arranged to measure the pressure in the low pressure chamber.

24. The method as claimed in claim 15, in which said second pressure changing device is included in a single-stroke pressure intensifier which comprises a low pressure chamber in which a low pressure piston is axially displaceable, a high pressure chamber being arranged on one side of the low pressure chamber and coaxially therewith, a high pressure piston being secured to the low pressure piston and being arranged axially displaceable in the high pressure chamber, the method further comprising the step of:

measuring the pressure in the low pressure chamber, thereby enabling the pressure in the pressure vessel to be calculated.

* * * * *